United States Patent [19]
Chung et al.

[11] Patent Number: 5,874,305
[45] Date of Patent: Feb. 23, 1999

[54] ANDROGEN-REPRESSED METASTATIC HUMAN PROSTATE CANCER CELL LINE

[75] Inventors: Leland W.K. Chung; Haiyen E. Zhau; Shi-ming Chang, all of Charlottesville, Va.

[73] Assignee: University of Virginia Patent Foundation, Charlottesville, Va.

[21] Appl. No.: 593,807

[22] Filed: Jan. 30, 1996

[51] Int. Cl.⁶ .................................................... C12N 5/00
[52] U.S. Cl. ........................................... 435/366; 435/325
[58] Field of Search .............................. 435/240.2, 325, 435/366, 4, 29

*Primary Examiner*—Leon B. Lankford, Jr.
*Attorney, Agent, or Firm*—Oblon, Spivak, McClelland, Maier & Neustadt, P. C.

[57] ABSTRACT

A new prostate cancer cell line is a continuous line of androgen-repressed metastatic prostate cancer cells. Androgen-repressed prostate cancer cells are linked with aggressive, malignant prostate cancer, in the identification and establishment of androgen-repressed prostate cancer cell lines, which are stable and continuous, allows the examination of therapeutic agents therefor, as well as identification of biological markers for the same.

9 Claims, 9 Drawing Sheets

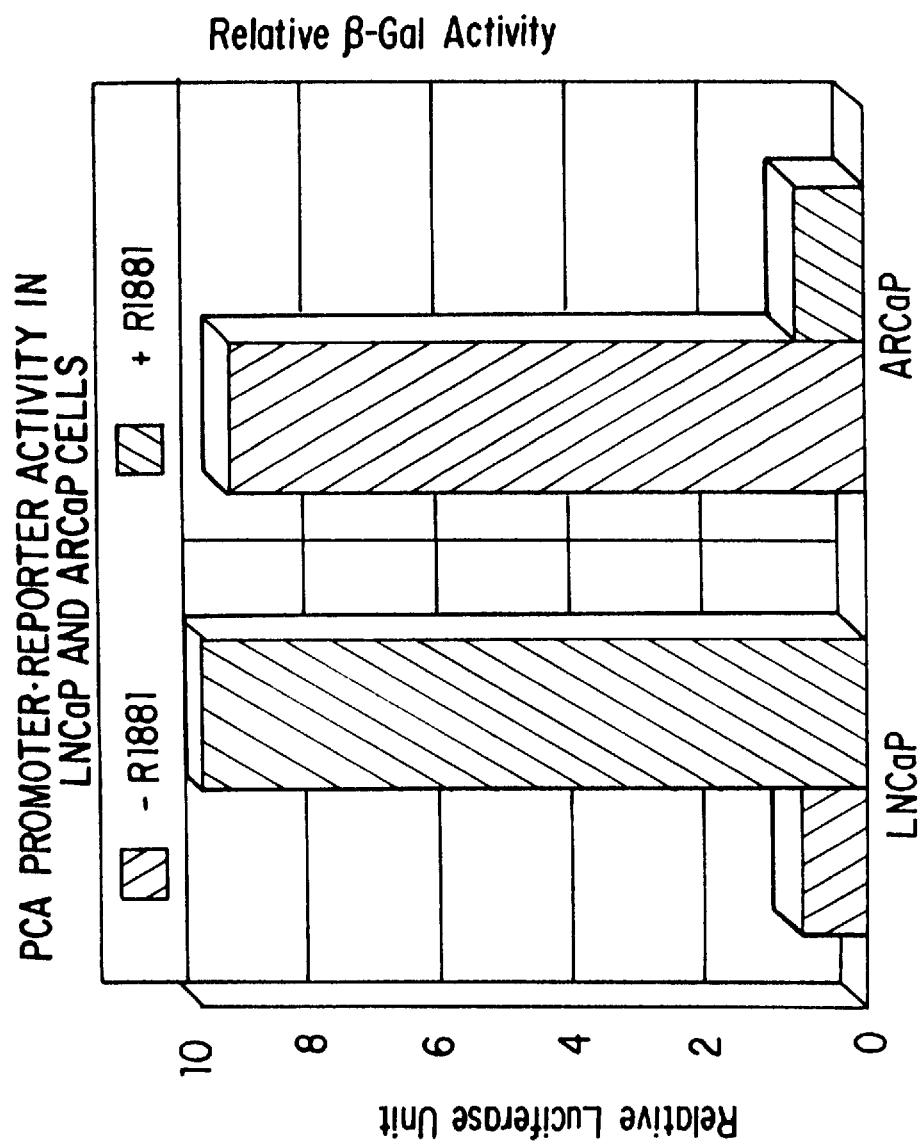

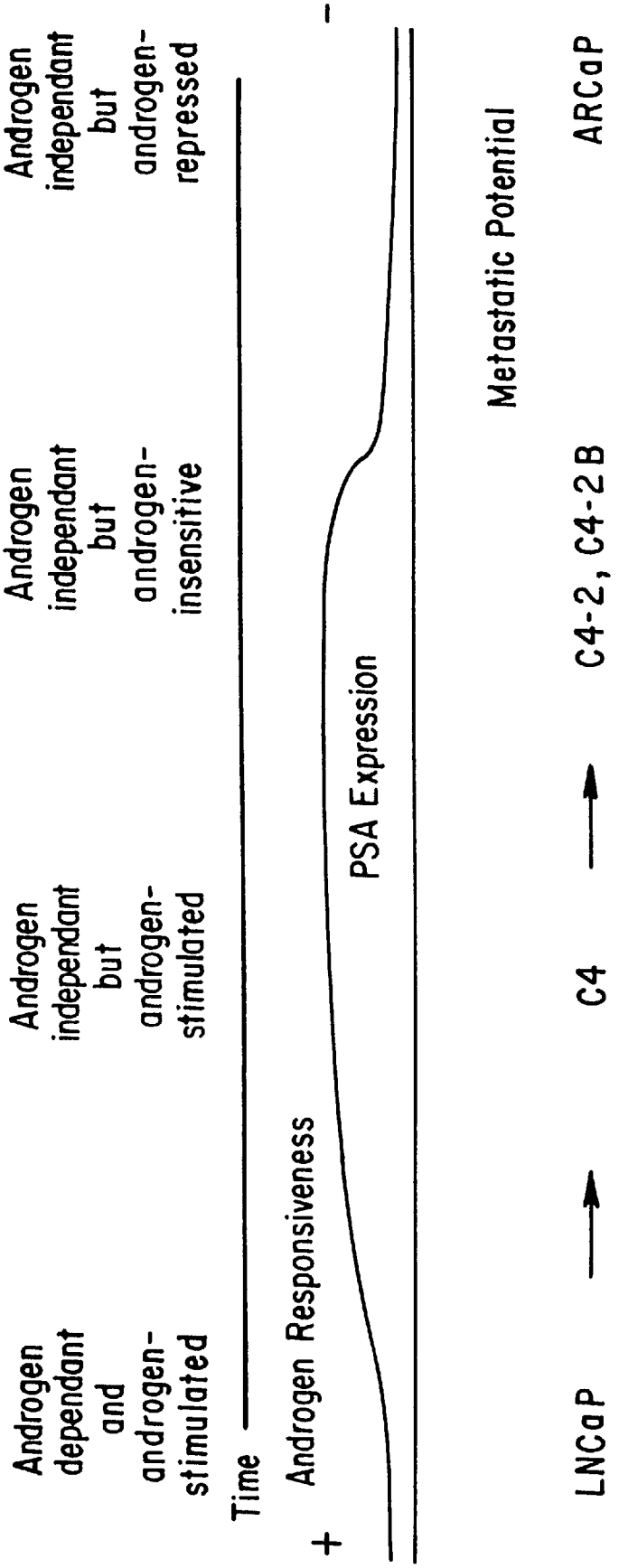

ANDROGEN-REPRESSED METASTATIC HUMAN PROSTATE CANCER CELL LINE

BACKGROUND OF THE INVENTION

1. Field of the Invention

This invention pertains to human prostate cancer. More specifically, the invention involves the establishment of androgen-repressed human prostate cancer cell lines, which may be used to identify biological markers to differentiate malignant and benign forms of prostate cancer. The cell line also provides a basis for screening therapeutic agents against advanced forms of human prostate cancer.

BACKGROUND OF THE PRIOR ART

Prostate cancer is the most common cancer diagnosed in the United States, the second leading cause of death due to cancer in males in the United States. Prostate cancer has been characterized as progressing from androgen-dependent cancer cells to androgen-independent cancer cells. Prior to applicants' invention, there was belief, but no substantial evidence, that a significant fraction of prostate cancer patients, perhaps above 20 percent of all patients, may further progress to a point where the cancer cells are androgen-repressed. Androgen-repressed phenotypes are believed characterized by more advanced and aggressive cell behavior, including proliferation and tendency to metastasize.

To be able to distinguish between aggressive, malignant cancers of this form, and benign prostate cancer, it is necessary to isolate the gene series responsible for the differentiation, which in turn requires identification of these advanced and aggressive prostate cancer cells. Further, identification of the genetic expression of these cells may allow the identification of biological markers which can be used to screen individuals for a propensity to the development of aggressive prostate cancer. Further, establishment of androgen-repressed prostate cancer cell lines is a prerequisite to effective in vitro and in vivo screening of therapeutic agents against these forms of prostate cancer.

Accordingly, the establishment of a continuous cell line of androgen-repressed metastatic prostate cancer cells remains an object of those of skill in the art.

SUMMARY OF THE INVENTION

A prostate cancer cell line, repressed by androgen and estrogen concentrations, has been demonstrated to metastasize to various organs when administered orthotopically and has been designated ARCaP. This cell line consists of both fast and slow-growing clones, successfully cloned by a soft agar method cloning system, conventional in the industry and which does not constitute an aspect of the invention.

The cell line was established from cells of clinical specimens recovered from the ascites fluid of a patient with widely disseminated prostate cancer.

The cancer cell line can be used as a screen, either in vitro, or, when administered to a host, in vivo, with therapeutic agents. Additionally, analysis of the genome should allow for identification of biological markers, as well as isolation of those fragments responsible for expression of the phenotypes observed.

The cell line is continuously available from the laboratories of the Department of Urology, University of Virginia, Charlottesville, Va. Additional cell lines can be prepared according to the methods described by the artisan. A deposit of the same cell lines is being made at the American Type Culture Collection, Rockville, Md., under Accession Number ATCC CRL-12277, deposited Jan. 24, 1997.

BRIEF DESCRIPTION OF THE DRAWINGS

FIG. 8 reflects transfected genetic expression induced or inhibited by androgen in the cells of the inventive cell line and LNCaP cells.

FIG. 9 is a graphical representation of a cell model of prostate cancer progression based on the inventive cell line.

DETAILED DESCRIPTION OF THE INVENTION

The inventive prostate cancer cell line clones, identified as ARCaP, were obtained by culturing cells recovered from clinical specimens from the ascites fluid of a patient with well progressed, widely metastasized prostate cancer. Similar cell lines may be obtained by culturing clinical specimens from other patients. Samples of ARCaP cell lines are available, without restriction, from the University of Virginia, Urology Department, Charlottesville, Va., through the inventors. The cell lines are monitored, and have been maintained, and are continuous from the original specimen. A deposit of the cell line may be accessed from the American Type Culture Collection, Rockville, Md., under Accession Number ATCC CRL-12277, deposited Jan. 24, 1997.

Figure 1:
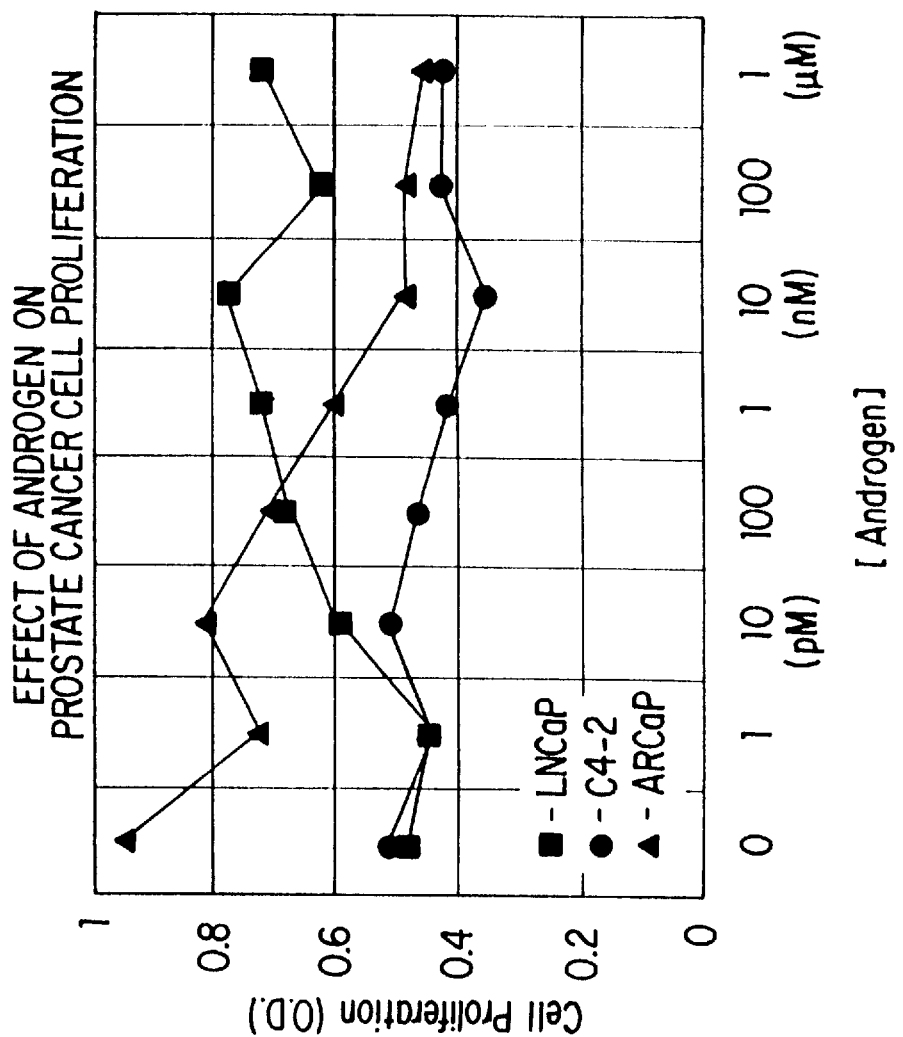
FIG. 1 reflects the effect of androgen concentration on proliferation of the prostate cancer cells of the invention, and two non-androgen-repressed cancer cell lines.

The cell line has been demonstrated to be repressed by both androgens and estrogens. FIG. 1 compares the effect of androgen on prostate cancer cell proliferation of the inventive cell line, compared with the androgen-dependent cell line LNCaP and androgen-independent C4-2 cells. As is reflected in FIG. 1, cell proliferation of ARCaP cells drops in response to increasing concentrations of androgen, whereas, as expected, LNCaP cells exhibit enhanced proliferation in the presence of enhanced amounts of androgen, and C4-2 cells are insensitive to androgen concentration in proliferation. It is of moment to note the relatively high cell proliferation rate of ARCaP cells in the absence of androgen.

FIG. 1 is a demonstration of in vitro confirmation of androgen sensitivity.

Figure 2:
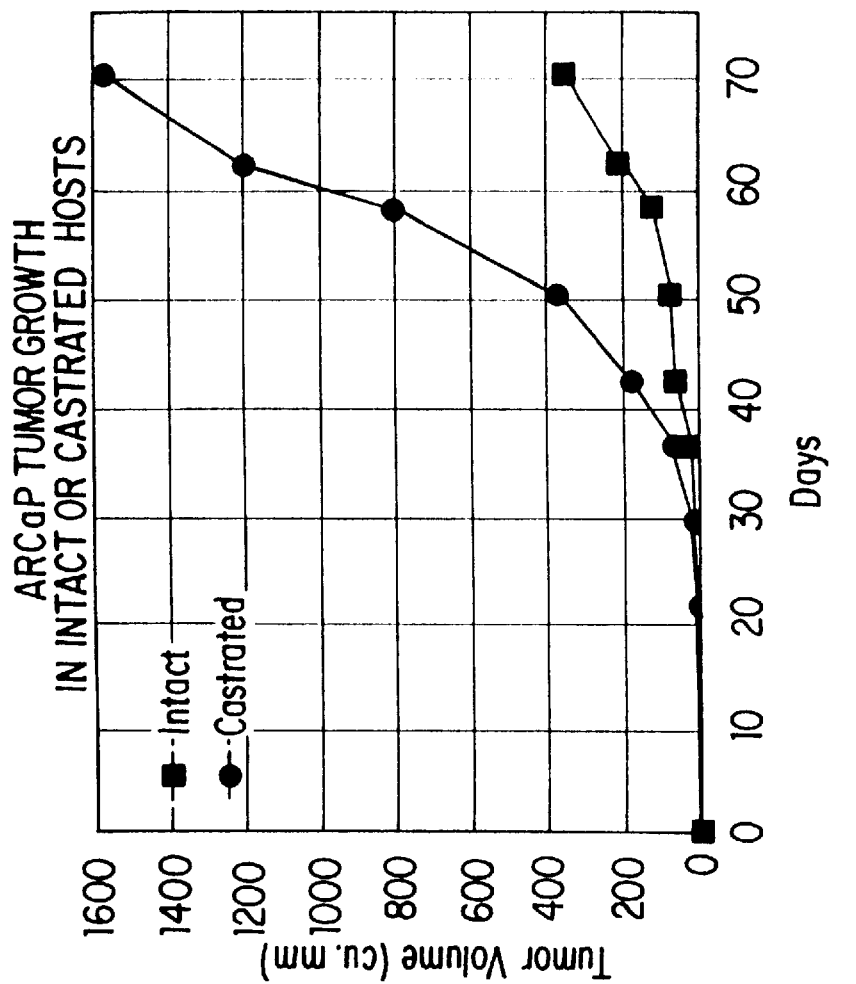
FIG. 2 is a graph reflecting tumor growth of the inventive cell line in castrated and non-castrated hosts, demonstrating the effect of androgen repression.
Figure 3:
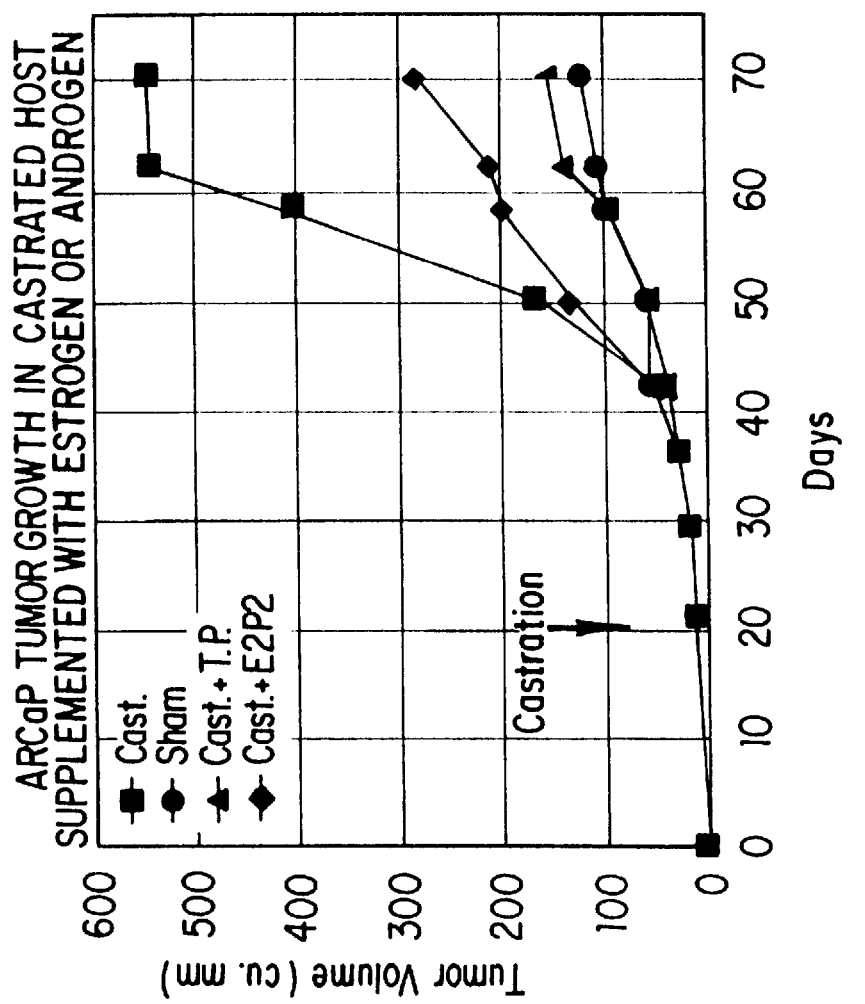
FIG. 3 is a graph demonstrating the impact of estrogen concentration on tumor growth of the inventive cell line.

Tests in intact or castrated hosts demonstrate the same androgen repression. FIG. 2 reflects dramatically accelerated tumor volume in castrated hosts, as opposed to intact hosts, the differential being observed about twenty days after orthotopic administration. Similarly, in vivo demonstration of estrogen and androgen dependence is reflected in FIG. 3.

The hosts for the in vivo experimentation are athymic nude mice.

Figure 4:
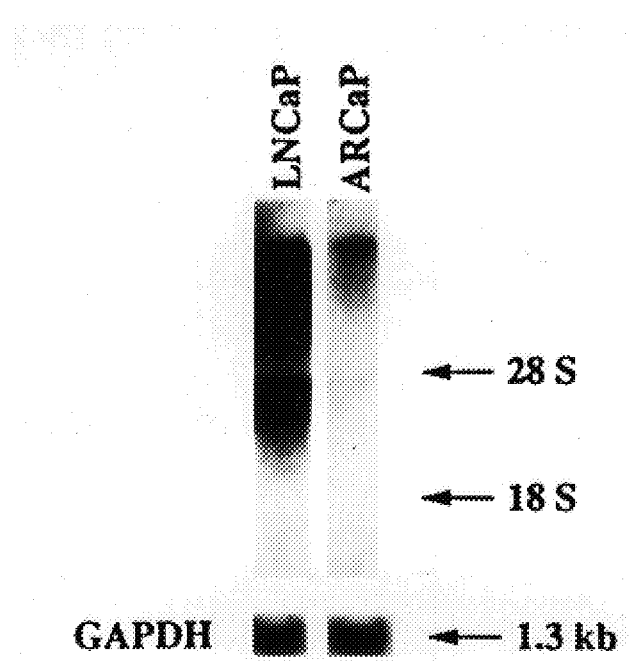
FIG. 4 is a Northern blot assay photograph demonstrating low levels of androgen receptor m-RNA in the inventive cell line.
Figure 5:
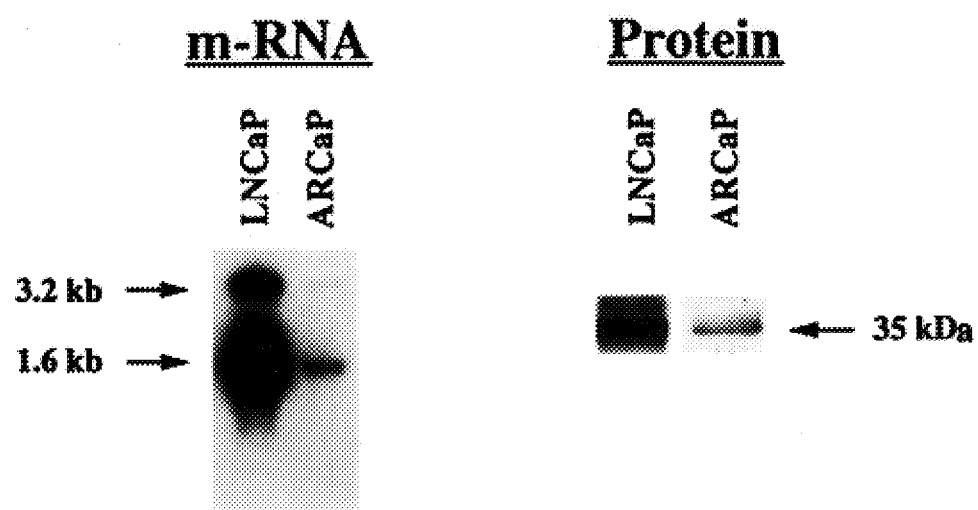
FIG. 5 is a blot assay demonstrating low levels of prostate-specific antigen m-RNA and protein in the cells of the inventive cell line.
Figure 6:
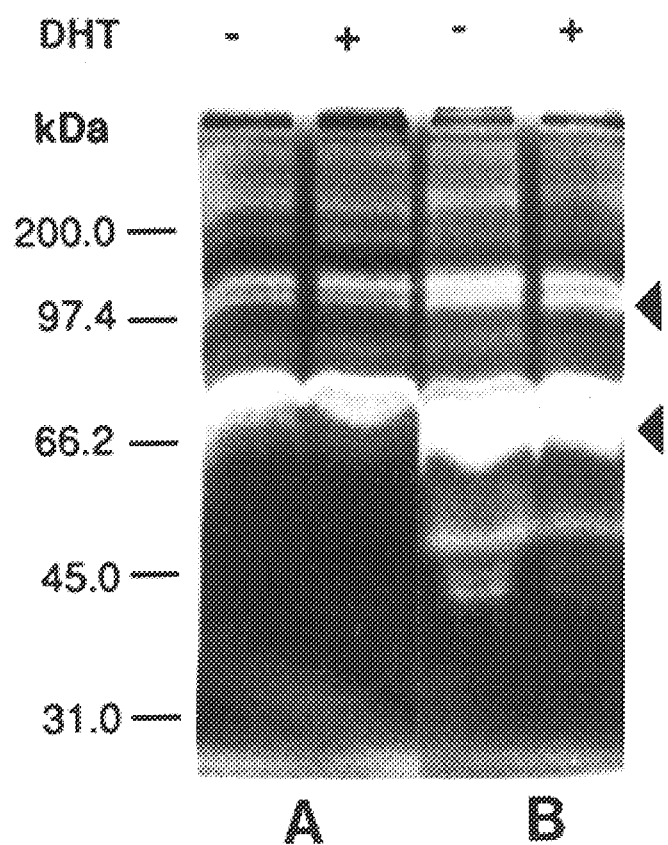
FIG. 6 reflects assay results demonstrating high levels of collagenase IV activity in the inventive cells and LNCaP cells, and expression in response to the presence of an androgen agonist (DHT).
Figure 7:
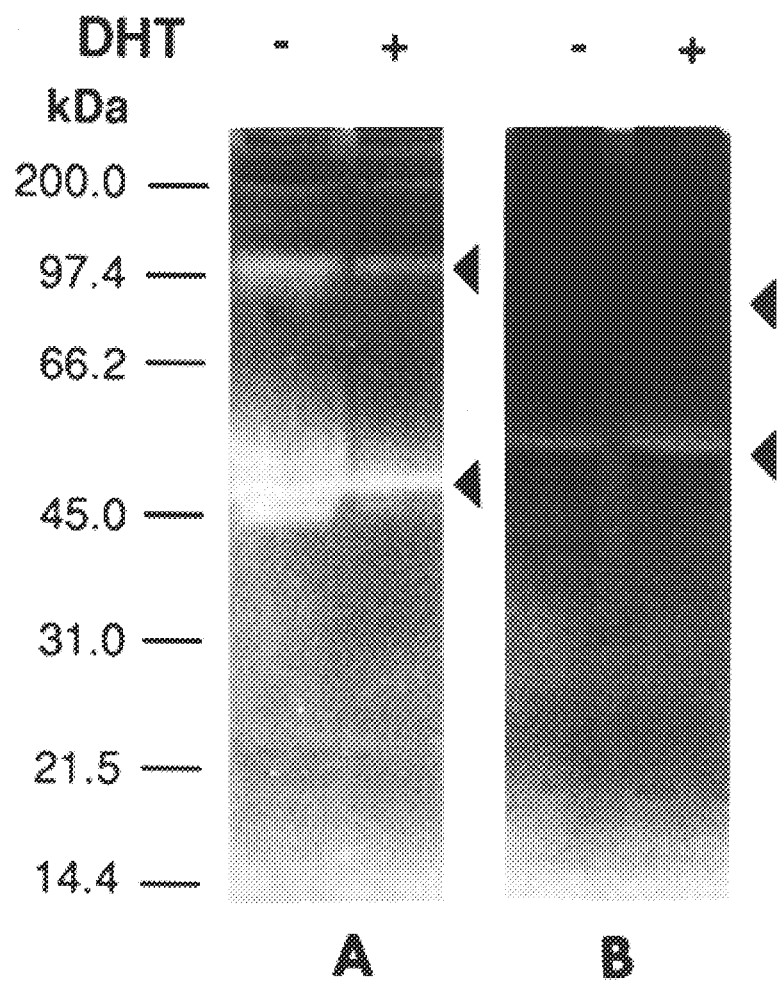
FIG. 7 reflects the results of an assay demonstrating stromolysin expression by cells of the inventive cell line, and its inhibition by DHT, an androgen agonist.

The androgen-repressed prostate cancer cells of the invention are characterized by markedly different expression characteristics. Thus, as illustrated in FIG. 4, ARCaP cells express a much lower level of androgen receptor as compared to prior art, widely available LNCaP prostate cancer cells, which are androgen stimulated. Similarly, the inventive cells express far lower levels of prostate-specific antigen, both PSA m-RNA and protein, as illustrated in FIG. 5. Further cell expression characteristics are seen in the secretion, by ARCaP cells, of large amounts of metalloproteinases, including collagenase IV, FIG. 6, and stromolysin, reflected in the assay of FIG. 7. In contrast, LNCaP cells do not secrete stromolysin. Consistent with the other observations, levels of these basement membrane-degradation enzymes appear repressed by the presence of androgen (DHT), an androgen agonist.

Further molecular differences between ARCaP cells and androgen-stimulated LNCap cells can be found in the differences of higher levels of expressed growth factor receptors (EGFR, c-met) oncogenes (c-erb B2/neu. c-met) and various neuroendocrines. The growth and metastatic profiles of ARCaP cells, set forth in Table 1, are distinct from prior androgen-stimulated and androgen-insensitive cell lines, and reflected in their cell expression differentials, Table 2.

TABLE 1

GROWTH OF METASTATIC PROFILES OF ARCaP CELLS

| ORGANS | INCIDENCE | |
|---|---|---|
| Prostate | 24/24 | (100%) |
| Lymph Nodes | 17/24 | (71%) |
| Bone | 4/24 | (17%) |
| Kidney | 5/24 | (21%) |
| Lung | 3/24 | (13%) |
| Liver | 2/24 | (8%) |

TABLE 2

COMPARATIVE IMMUNOHISTOCHEMICAL EXPRESSION OF NEUROENDOCRINE FACTORS, NEU, EGFR, AND AR BY LNCaP AND ARCaP CELLS

| MARKERS | LNCaP | ARCaP |
|---|---|---|
| Serotonin | ++ | ++ |
| Bombesin | + | ++ |
| Substance P | ++ | + |
| Neurophysin | +++ | + |
| c-erb/B neu | + | +++ |
| EGFR | ++ | ++++ |
| AR | ++ | + |

Further distinctions between the cell line that is the subject of this invention and the LNCaP cell line, also available from the American Type Culture Collection, is reflected in molecular analysis. In the trial reflected in FIG. 8, adenoviral-p64 PSA promotor-β-galactosidase was delivered to ARCaP. Reporter activity (galactosidase activity) was markedly suppressed by addition of androgen, strongly suggesting that expression of PSA, a classic androgen-stimulated gene, is also suppressed in ARCaP cells by androgen. As a positive control, PSA-promoter-luciferase activities were greatly stimulated by androgen addition when transfected to the androgen-stimulated LNCaP line. This molecular analysis is reflected in FIG. 8.

The value of the inventive cell line is most easily seen in terms of FIG. 9, which presents a cellular model of the progression of human prostate cancer. Thus, as the disease progresses from androgen-dependent and androgen-stimulated cells, such as LNCaP, through various stages to androgen-independent, androgen-repressed cells such as those of the invention, therapeutic treatment, as well as testing, must change as well. It is of particular note that metastatic potential increases dramatically as the disease progresses to the androgen-repressed stage characterized by ARCaP cells. The inventive cell lines lend themselves to a variety of utilities. Perhaps most importantly, the cells provide both an in vitro and in vivo test screen for therapeutic agents. Therapeutic agents that are intended to act against aggressive, rapidly proliferating cancer cells capable of marked metastasizing must be effective against cells such as those of the ARCaP line. Preliminary in vitro testing, followed by in vivo testing in mammalian model hosts, such as athymic nude mice infected with the cell line, gives a reliable, predictive model of efficacy in humans.

Additionally, genetic markers characterizing these cells, in light of their phenotypic differences from other cancer cells, should be susceptible of isolation by conventional means. This will provide an additional means for screening patients in this stage of the disease, together with those with a propensity to develop this stage of prostate cancer.

As noted above, the specific cell line described, available and deposited, ARCaP, was obtained through conventional cell isolation and culturing processes. Specifically, a patient with marked metastatic prostate cancer progression was the source of ascites fluid samples. The samples were collected, centrifuged gently, and the cells obtained therefrom collected. The cells were cultured according to standard methods. In particular, ascites fluid centrifuged materials tends to contain a mixture of fibroblast and epithelial cells. Fibroblast cells have a tendency to overgrow the culture, while 90 percent of all cancer cells come from epithelial cells. Thus, a repeated culturing process, to promote epithelial cell growth and isolation was undertaken, using T-media, although other media are suitable. Other methods of isolation of similar sources of androgen-repressed metastatic prostate cancer cells can be identified, and similarly obtained, without exercise of inventive faculty.

The above-described invention has been set forth in terms both generic, and exemplary. Examples are not intended to be limiting unless so indicated, and alterations and modification will occur to those of ordinary skill in the art without departing from the scope of the invention, particularly with respect to methods of culture, specific identity of cell lines, and the like. Such alternatives remain within the scope of the invention, save as limited by the claims set forth below.

What is claimed:

1. A continuous cell line of androgen-repressed metastatic human prostate cancer cells, having the androgen-repression characteristics of CRL-12277.

2. The cell line of claim 1, wherein said cell line comprises both fast-growing clones and slow-growing clones.

3. The cell line of claim 1, wherein said cell line contains fast-growing clones.

4. The cell line of claim 1, wherein said cell line contains slow-growing clones.

5. The cell line of claim 1, wherein said cell line secretes stromolysin.

6. The cell line of claim 1, wherein said cells express greater levels of growth factor receptors and oncogenes than androgen-stimulated prostate cancer cell lines.

7. The cell line of claim 1, wherein said cell line is ARCaP.

8. A method of screening potential therapeutic agents for the treatment of androgen-repressed metastatic prostate cancer, comprising administering said potential therapeutic agent, to a cell line of androgen-repressed metastatic prostate cancer cells, culturing said cells, and determining whether said therapeutic agent inhibits the growth of said cells, proliferation of said cells or tendency of said cells to metastasize.

9. A method of screening potential therapeutic agents for the treatment of metastatic prostate cancer in vivo comprising administering androgen-repressed prostate cancer cells to a mammalian host, allowing said cells to proliferate in said host, and administering said therapeutic agent to said host, and examining said host to determine whether said therapeutic agent inhibits the growth, proliferation or metastasizing of said prostate cancer cells.

* * * * *

UNITED STATES PATENT AND TRADEMARK OFFICE
CERTIFICATE OF CORRECTION

PATENT NO. : 5,874,305
DATED : February 23, 1999
INVENTOR(S) : Leland W.K. Chung et al.

It is certified that error appears in the above-identified patent and that said Letters Patent is hereby corrected as shown below:

Column 1,
The following paragraph is inserted immediately after the title:

U.S. Government Rights
This invention was made with United States Government support under Grant Nos. CA57361, CA93037, and DK47596, awarded by the National Institutes of Health. The United States Government has certain rights in the invention.

Signed and Sealed this

Fifth Day of March, 2002

Attest:

JAMES E. ROGAN
Attesting Officer
Director of the United States Patent and Trademark Office